(12) United States Patent
Du et al.

(10) Patent No.: US 11,952,518 B2
(45) Date of Patent: Apr. 9, 2024

(54) SYNTHESIS AND APPLICATION OF FLUORESCENT DYE WITH PHENANTHRIDINE AND BENZOTHIAZOLE CONJUGATED

(71) Applicant: Beijing Fluorescence Biotechnology Co. Ltd, Beijing (CN)

(72) Inventors: Chimin Du, Beijing (CN); Sophia Du, Beijing (CN)

(73) Assignee: Beijing Fluorescence Biotechnology Co. Ltd, Beijing (CN)

( * ) Notice: Subject to any disclaimer, the term of this patent is extended or adjusted under 35 U.S.C. 154(b) by 9 days.

(21) Appl. No.: 17/730,528

(22) Filed: Apr. 27, 2022

(65) Prior Publication Data

US 2023/0257647 A1 Aug. 17, 2023

(30) Foreign Application Priority Data

Feb. 17, 2022 (CN) .......................... 202210145256.6

(51) Int. Cl.
| | | |
|---|---|---|
| C07D 417/14 | (2006.01) |
| C09B 57/00 | (2006.01) |
| C09K 11/06 | (2006.01) |
| C12Q 1/6809 | (2018.01) |
| G01N 1/30 | (2006.01) |

(52) U.S. Cl.
CPC ............ *C09K 11/06* (2013.01); *C07D 417/14* (2013.01); *C09B 57/00* (2013.01); *C12Q 1/6809* (2013.01); *G01N 1/30* (2013.01); *C09K 2211/1007* (2013.01); *C09K 2211/1022* (2013.01); *G01N 2001/302* (2013.01)

(58) Field of Classification Search
CPC .............................. C09K 11/06; C07D 417/14
See application file for complete search history.

(56) References Cited

FOREIGN PATENT DOCUMENTS

| | | |
|---|---|---|
| CN | 111349091 A | 6/2020 |
| CN | 112521383 A | 3/2021 |

*Primary Examiner* — Shawquia Jackson

(57) ABSTRACT

The disclosure relates to the field of fluorescent dyes, and provides a fluorescent dye with phenanthridine and benzothiazole conjugated. The fluorescent dye has the following structural formula:

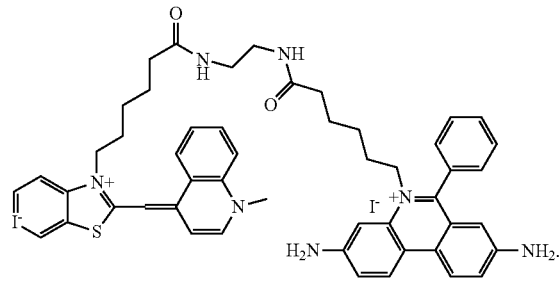

Through the above technical solution, the problems in the prior art that the fluorescent dye is susceptible to interference from other charged substances in a solution when detecting DNA so as not to be simultaneously applied to a blue light meter and an ultraviolet gel imager are solved.

2 Claims, 12 Drawing Sheets

SYNTHESIS AND APPLICATION OF FLUORESCENT DYE WITH PHENANTHRIDINE AND BENZOTHIAZOLE CONJUGATED

CROSS REFERENCE TO RELATED APPLICATIONS

This application claims foreign priority of Chinese Patent Application No. 202210145256.6, filed on Feb. 17, 2022 in the China National Intellectual Property Administration, the disclosures of all of which are hereby incorporated by reference.

TECHNICAL FIELD

The disclosure belongs to the field of fluorescent dyes, and relates to synthesis and application of a fluorescent dye with phenanthridine and benzothiazole conjugated.

BACKGROUND OF THE PRESENT INVENTION

A fluorescent dye refers to a substance that can emit another light wave whose wavelength is larger than a wavelength of absorption light after absorbing a light wave having a certain wavelength, which comes into a visible light wave with a longer wavelength after absorbing visible light and ultraviolet light to be reflected. It is a widely used fluorescent marker, is also called a fluorescent probe, has the advantages of fast detection speed, good repeatability, less sample amount, no radiation and the like, and can be used for detection of DNA, proteins, enzymes, metal ions, etc.

When the fluorescent dye is used for detection of DNA in the Nucleic Acid Gel Stain and PCR, a substrate forms a composite together with the fluorescent dye through a static interaction force between the substrate and the fluorescent dye. However, there is a drawback for detection of DNA by using the static interaction force, that is, the fluorescent dye is susceptible to interference from other charged substances in a solution so as not to be simultaneously applied to a blue light meter and an ultraviolet gel imager.

SUMMARY OF PRESENT INVENTION

The disclosure provides synthesis and application of a fluorescent dye with phenanthridine and benzothiazole conjugated, solving the problems in the prior art that the fluorescent dye is susceptible to interference from other charged substances in a solution so as not to be simultaneously applied to a blue light meter and an ultraviolet gel imager for the Nucleic Acid Gel Stain.

The technical solution of the disclosure is realized as follows:

Provided is a fluorescent dye with phenanthridine and benzothiazole conjugated, wherein the fluorescent dye has the following structural formula:

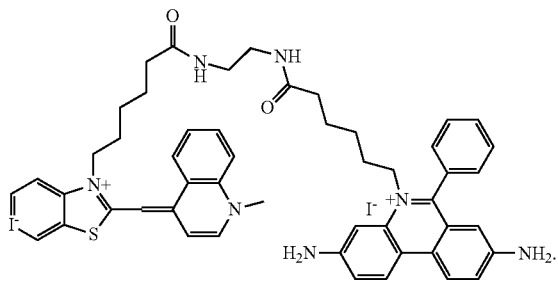

Provided is application of the above fluorescent dye, wherein the fluorescent dye is used for polymerase chain reaction, nucleic acid gel electrophoresis dyes, textile printing and dyeing, proteins and biological macromolecule staining.

Provided is synthesis of the above fluorescent dye, comprising the following steps:

S1, reacting a compound of formula 1 with methyl iodide for 4 h at 210° C. under the protection of nitrogen to prepare a compound of formula 3;

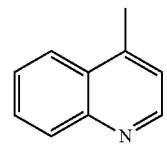

1

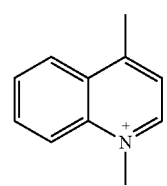

3

S2, dissolving a compound of formula 4 and 6-bromo-1-hexanoic acid into absolute ethyl alcohol under the protection of nitrogen, heating to 35° C. under the protection of nitrogen, and reacting for 4 h so as to prepare a compound of formula 6;

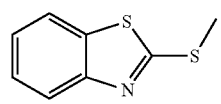

4

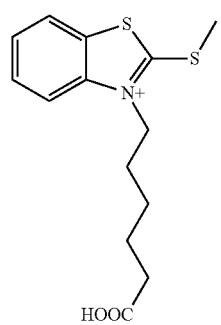

6

S3, dissolving the compound of formula 3 and the compound of formula 6 into ethyl alcohol, adding triethylamine under the protection of nitrogen, and reacting for 3 h to prepare a compound of formula 7;

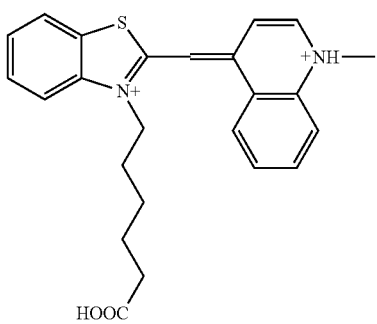

7

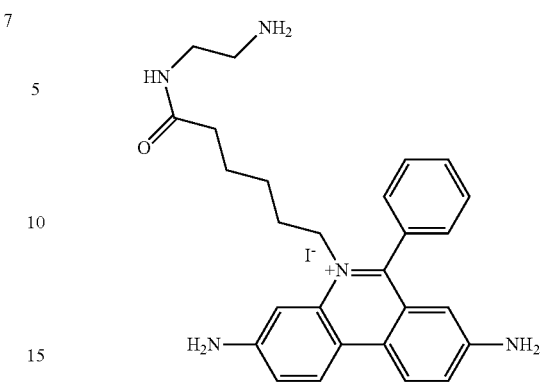

11

S4, dissolving the compound of formula 7 and 2-succinylimido-1,1,3,3-tetramethylurea tetrafluoroborate into acetonitrile, adding triethylamine, and reacting for 4 h to prepare an acetonitrile solution of a compound of formula 8;

S6, dissolving the compound of formula 11 into DMF, adding the acetonitrile solution of the compound of formula 8, and reacting for 12-16 h to obtain the fluorescent dye with phenanthridine and benzothiazole conjugated.

The disclosure has a working principle and beneficial effects.

1. In the disclosure, provided is a fluorescent dye with phenanthridine and benzothiazole conjugated, this fluorescent dye is not interfered by other charged substances in the solution when detecting DNA, thereby overcoming the disadvantages existing when the fluorescent dye in the prior art utilizes the static interaction force for detection, significantly improving an ability of the fluorescent dye to distinguish single/double stranded DNA molecules and increasing the detection sensitivity of DNA, and implementing simultaneous use for nucleic acid electrophoresis staining under a blue light meter and an ultraviolet gel imager.

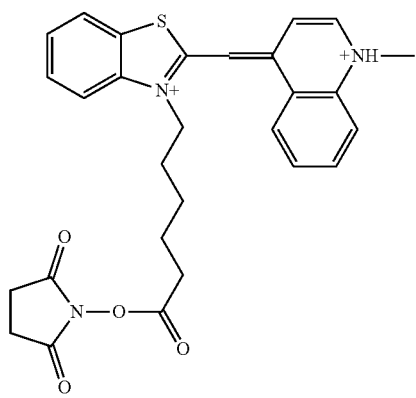

8

2. In the disclosure, the fluorescent dye with phenanthridine and benzothiazole conjugated has stable performances, is suitable for quantitative PCR and nucleic acid electrophoresis staining under the blue light meter and the ultraviolet gel imager as well, can be used for polymerase chain reaction, nucleic acid gel electrophoresis dyes, textile printing and dyeing, proteins and biological macromolecule staining.

3. In the disclosure, the fluorescent dye with phenanthridine and benzothiazole conjugated prepared by using phenanthridine and benzothiazole as raw materials through a series of reactions is high in product purity and stable in performances.

S5, dissolving a compound of formula 9 into DMF, adding 2-succinylimido-1,1,3,3-tetramethylurea tetrafluoroborate, stirring for 30 min, then adding triethanolamine, reacting for 30 min at 20-25° C., adding ethanediamine, and reacting for 12-16 h to prepare a compound of formula 11; and

DESCRIPTION OF THE DRAWINGS

The disclosure will be further described in detail in combination with drawings and specific embodiments below.

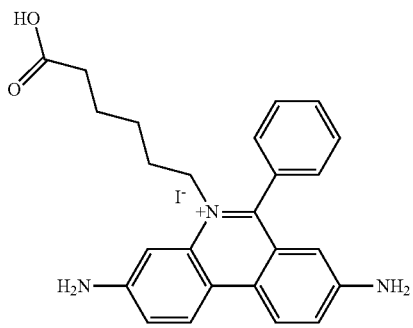

9

Figure 7:
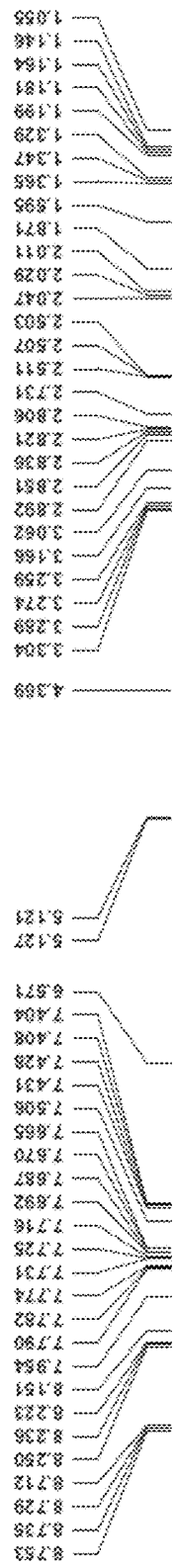
Figure 7:
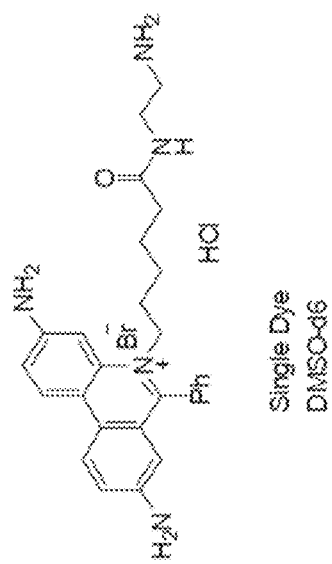
Figure 7:
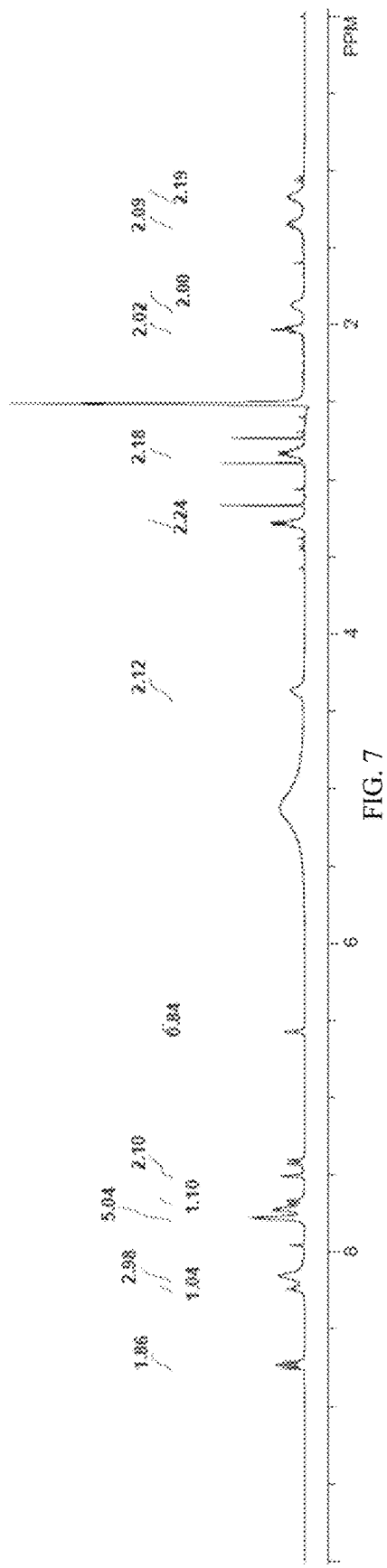

FIG. 7 is an H NMR spectrum of compound 11 according to the disclosure.

Figure 8:
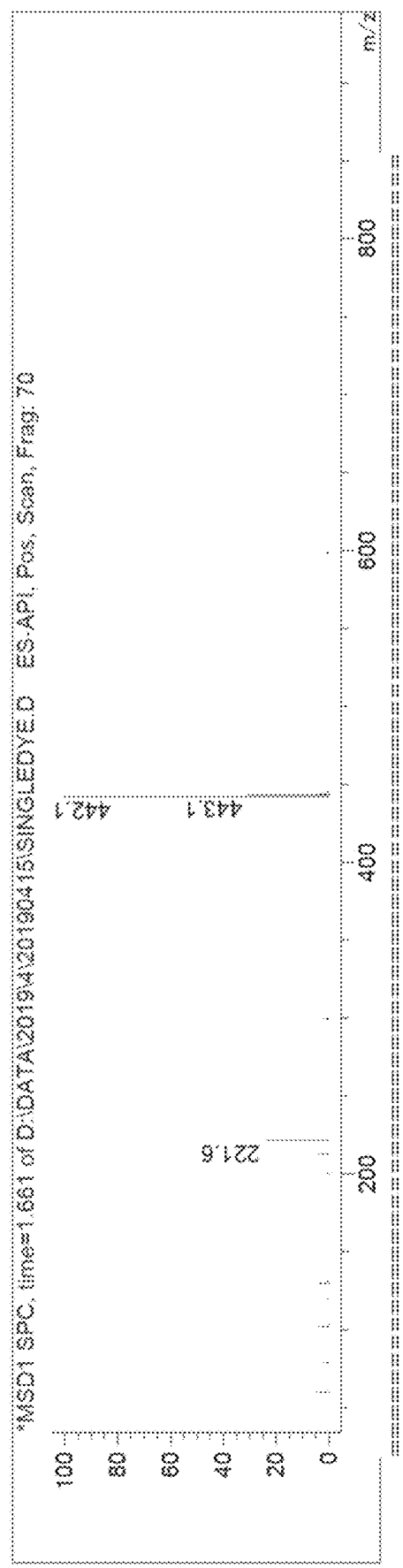

FIG. 8 is a mass spectrum of compound 11 according to the disclosure.

Figure 9A:
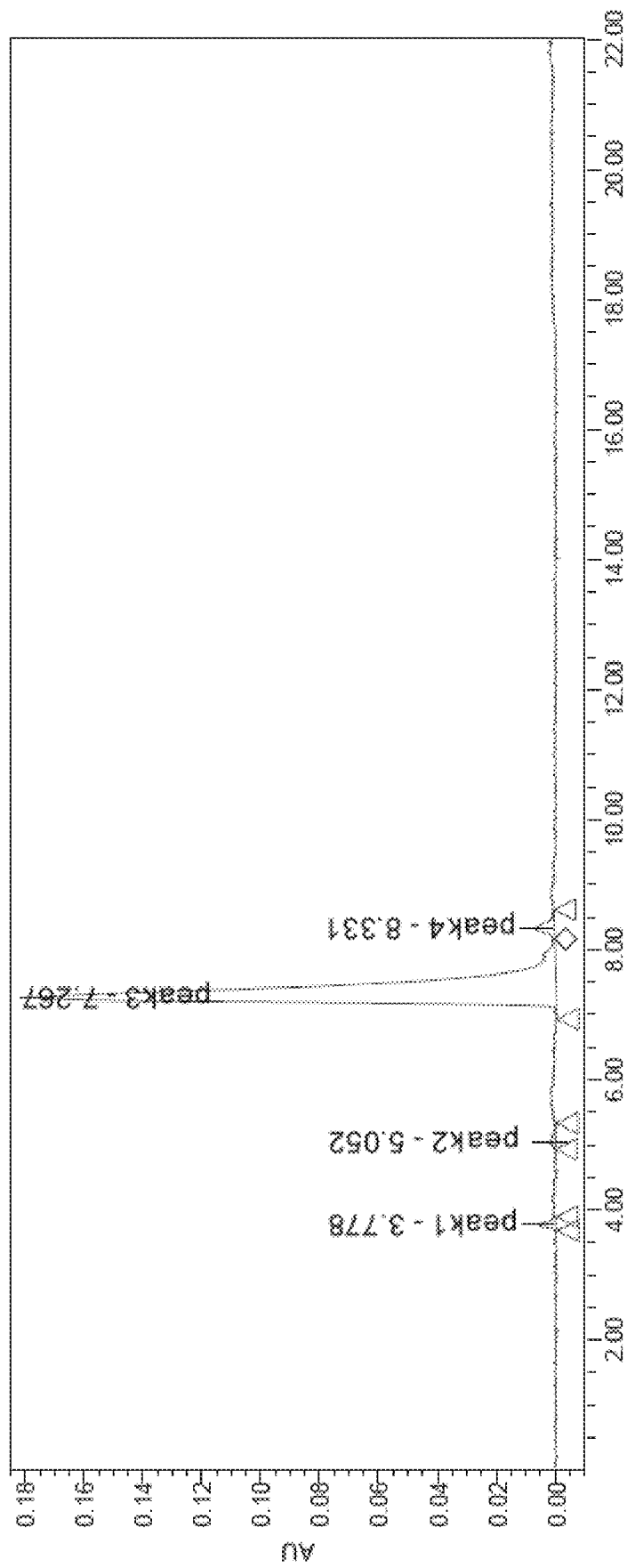

FIG. 9A is a part of a high performance liquid chromatography (HPLC) of fluorescent dye SafeStain according to the disclosure.

Figure 9B:
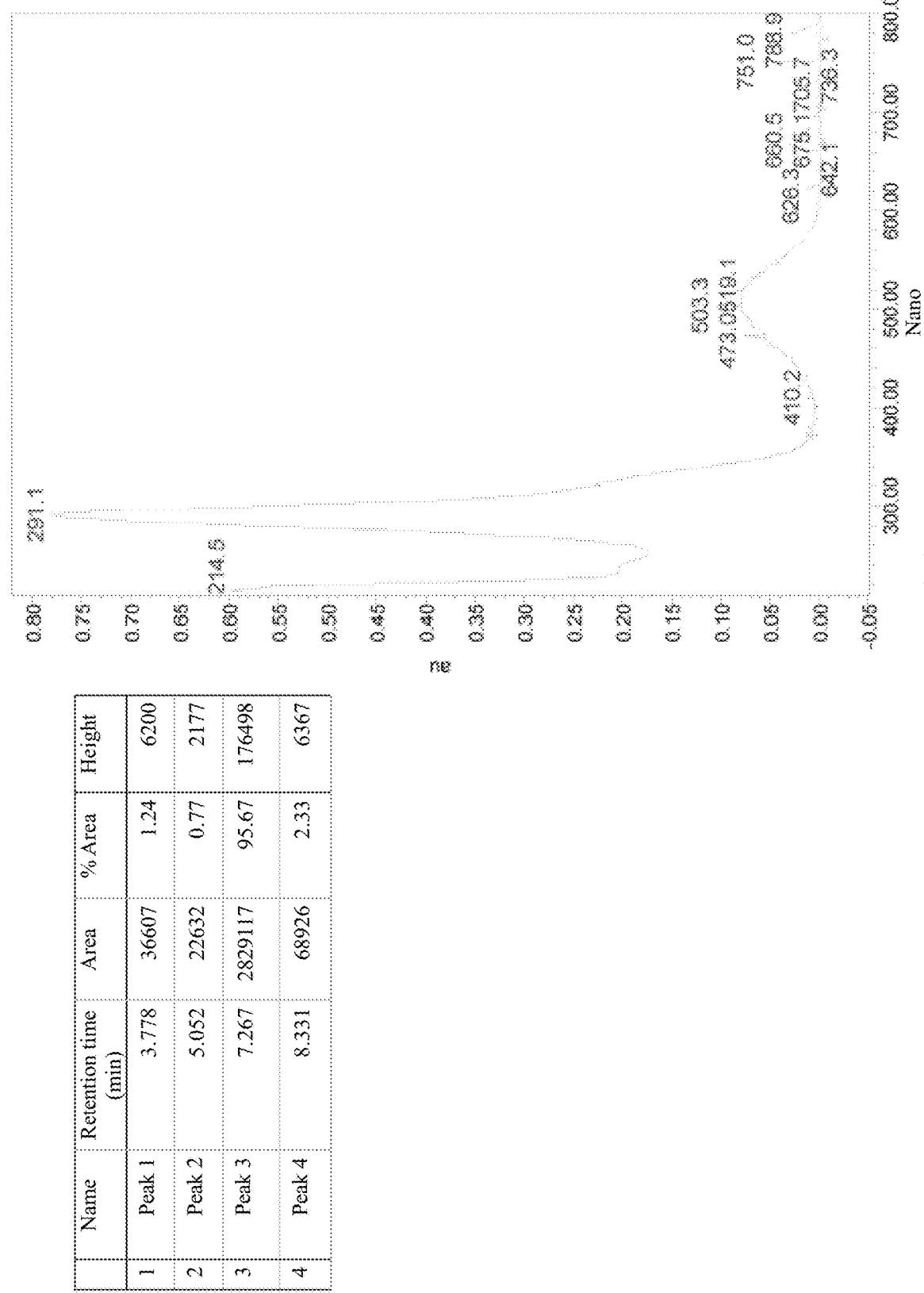

FIG. 9B is another part of a high performance liquid chromatography (HPLC) of fluorescent dye SafeStain according to the disclosure.

Figure 10:
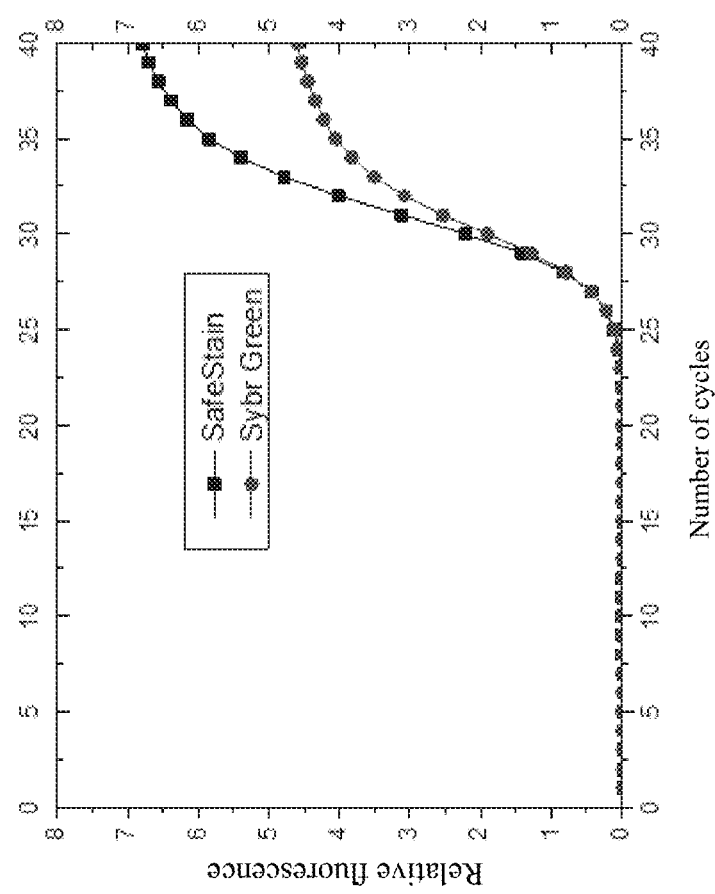

FIG. 10 is a real-time fluorescence quantitative PCR amplification curve electrophoretogram of fluorescent dye SafeStain according to the disclosure.

Figure 11:
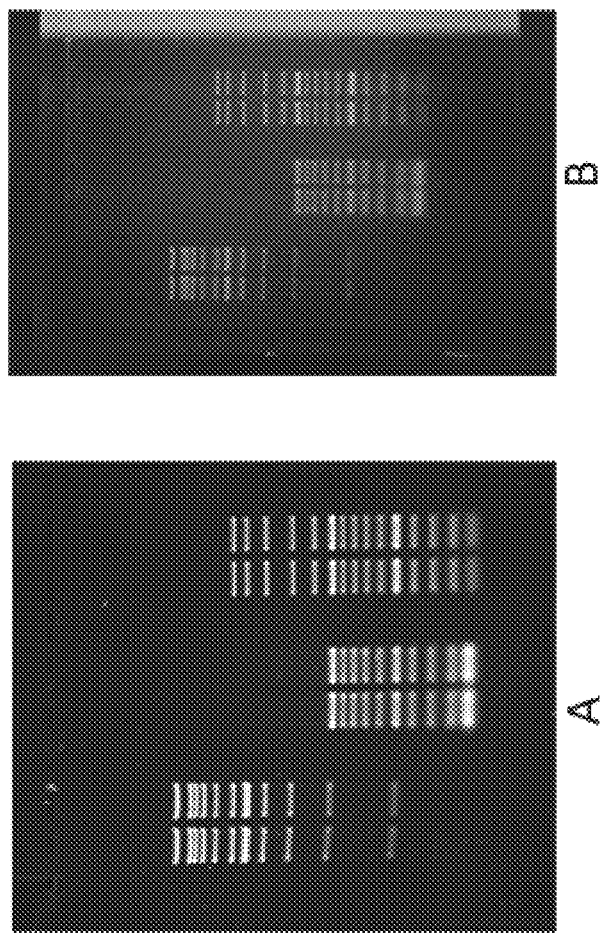

FIG. 11 is an electrophoretogram of fluorescent dye SafeStain under a UV Gel imager and a blue light gel imager according to the disclosure, wherein FIG. A is an electrophoretogram of fluorescent dye SafeStain under the UV Gel imager, and FIG. B is an electrophoretogram of fluorescent dye SafeStain under the blue light gel imager.

DETAILED DESCRIPTION OF PREFERRED EMBODIMENTS

The technical solution in embodiments of the disclosure will be clearly and completely described in combination with examples, obviously, the described embodiments are only a part of embodiments of the disclosure but not all the embodiments. Based on the embodiments of the disclosure, other embodiments obtained by those of ordinary skill in the art without creative efforts are all included within the protective scope of the disclosure.

Example 1

A fluorescent dye with phenanthridine and benzothiazole conjugated has a structural formula as follows:

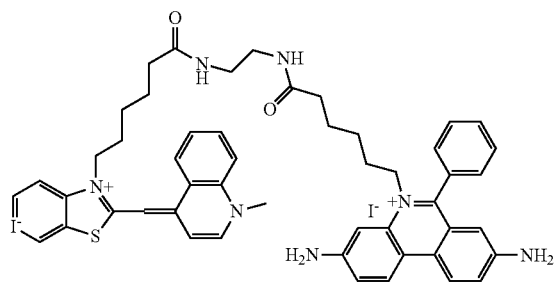

Figure 1:
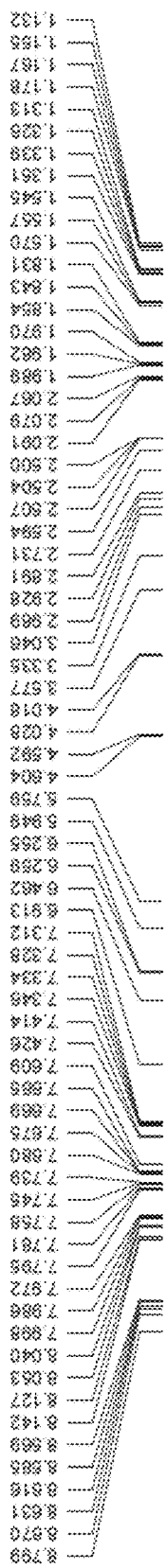
FIG. 1 is an H NMR spectrum of fluorescent dye SafeStain according to the disclosure.
Figure 1:
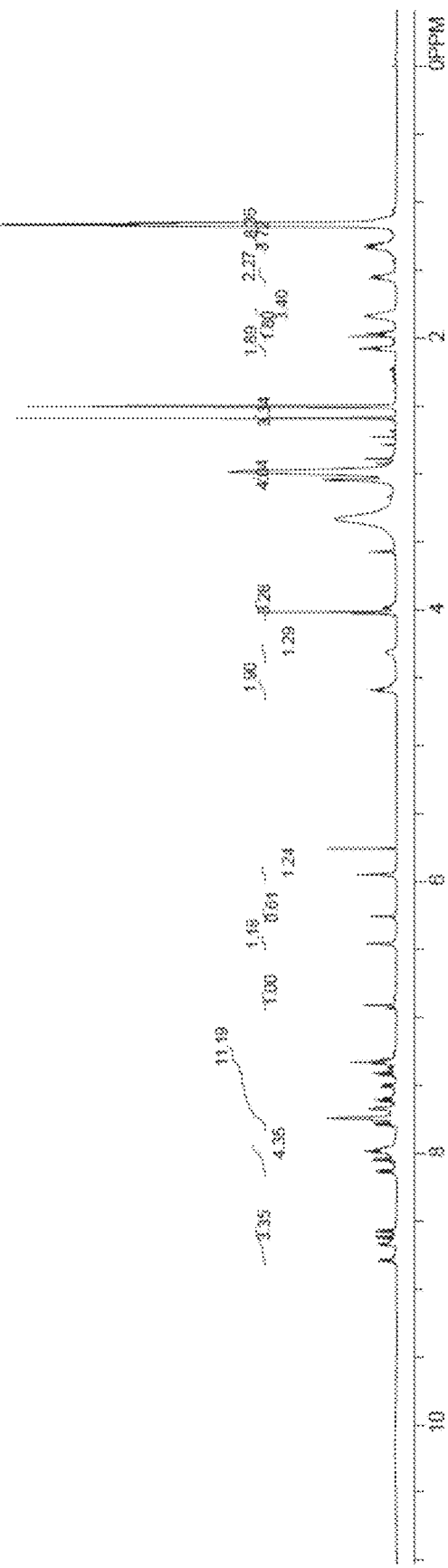
Figure 2:
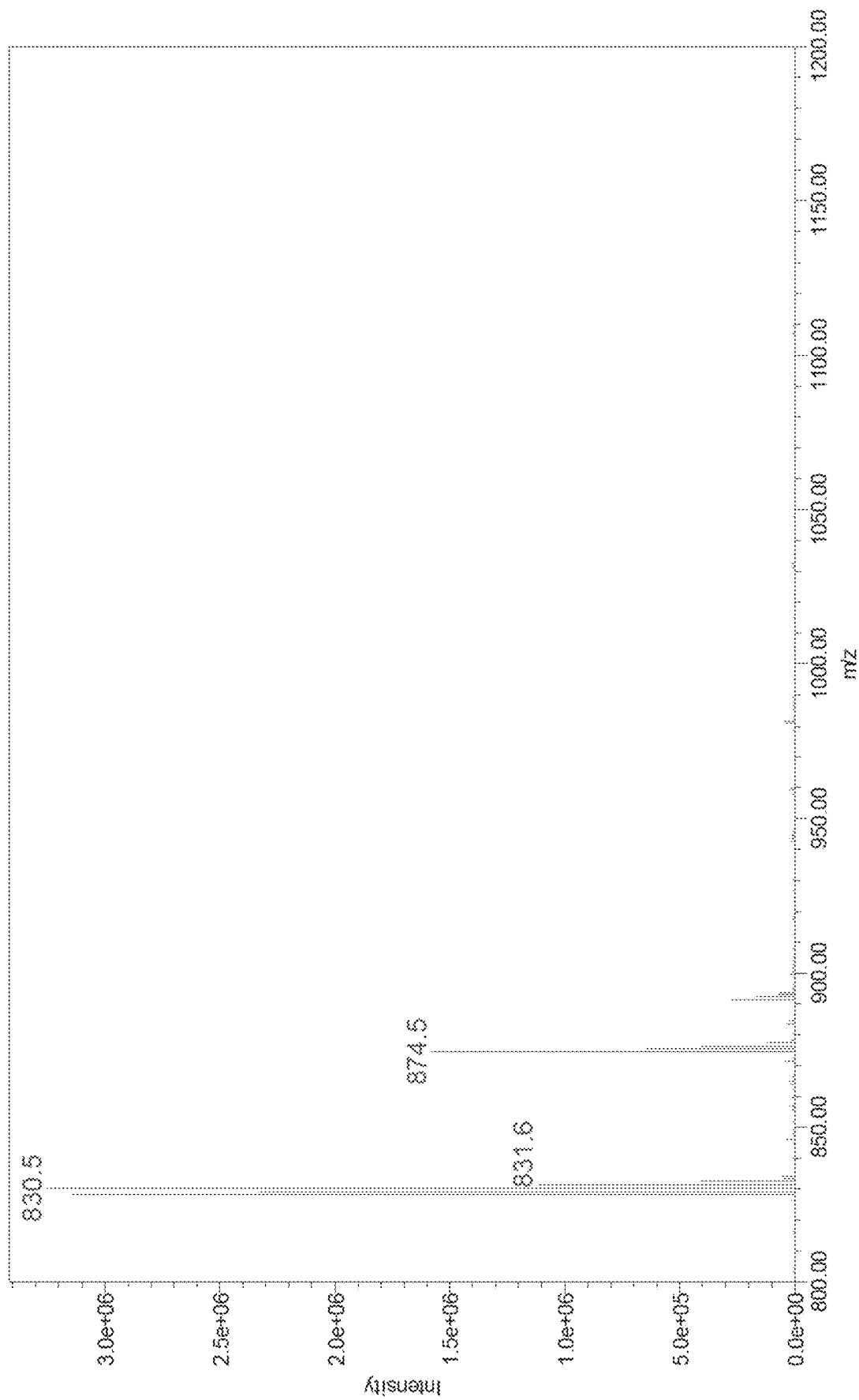
FIG. 2 is a mass spectrum of fluorescent dye SafeStain according to the disclosure.

The H NMR spectrum of the fluorescent dye is shown in FIG. 1. Test conditions are as follows: $^1$H NMR (400 MHz, $d_6$-DMSO);

The mass spectrum of the fluorescent dye is shown in FIG. 2, ESI-MS: experimental value m/z=831.6.

Example 2

A method for preparing the fluorescent dye in example 1 comprises the following steps:

S1, Synthesis of Compound 3

54.5 g of compound 1 and 112 g of methyl iodide (compound 2) were added into a 500 mL three-neck bottle, the above mixed solution was protected with nitrogen, heated to 210° C. and reacted for 4 h, thin-layer chromatography (TLC) detection was performed, and the reaction was completed; a reaction solution was cooled to room temperature, methanol was added into the reaction solution, the reaction solution was pulped by stirring and filtered, and a filter cake was washed with methanol to obtain 90 g of while solid, that is, compound 3, with a yield of 91.8%;

A reaction equation is as follows:

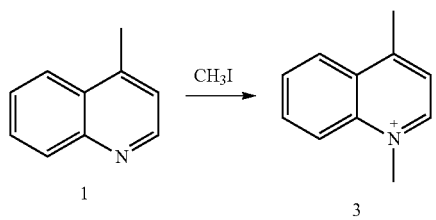

S2, Synthesis of Compound 6

30 g of compound 4 and 50 g of 6-bromo-hexanoic acid (compound 5) were added into a 250 ml three-neck bottle, the above mixed solution was protected with nitrogen, heated to 35° C. and reacted for 4 h, TLC detection was performed, and the reaction was ended; a reaction solution was cooled to room temperature, ethyl alcohol was added into the reaction solution, the reaction solution was pulped by stirring and filtered, a filter cake was washed with ethyl acrylate to obtain a light yellow solid, and the obtained light yellow solid was pulped with ethyl alcohol and then filtered to obtain 55 g of white powder, that is, compound 6, with a yield of 99.5%; a reaction equation is as follows:

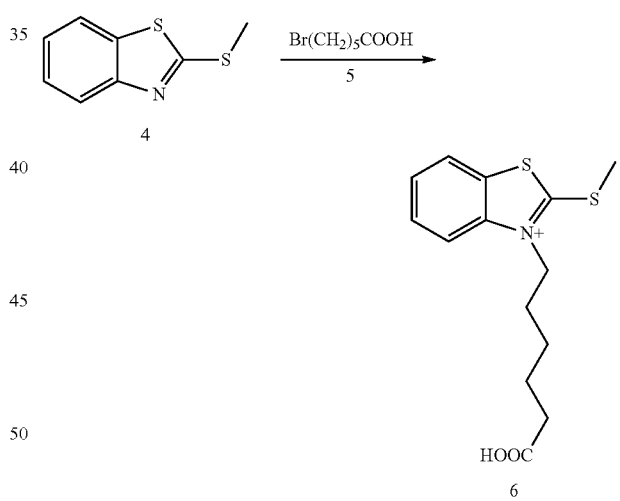

S3, Synthesis of Compound 7

30 g of compound 3 and 36 g of compound 6 were dissolved into 400 mL of absolute ethyl alcohol, the above mixed solution was protected with nitrogen, 19 mL of triethylamine was slowly dropwise added at room temperature, a reaction solution was black and then red, the reaction solution was stirred for 3 h, then 1 L of water was added at room temperature, then the resulting solution was continued to stir for 1 h and react, then the reaction solution was filtered, a filter cake was pulped with 100 mL of methanol and then filtered, and the filter cake was dried in vacuum to obtain 28 g of compound 7, with a yield of 77.8%;

A reaction equation is as follows:

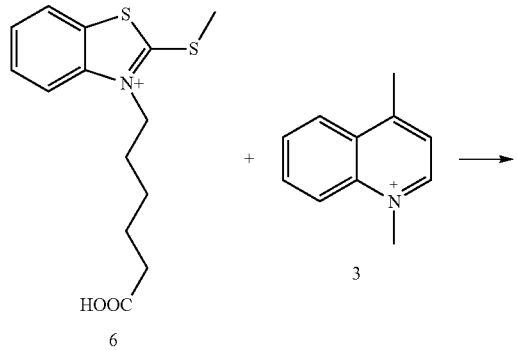

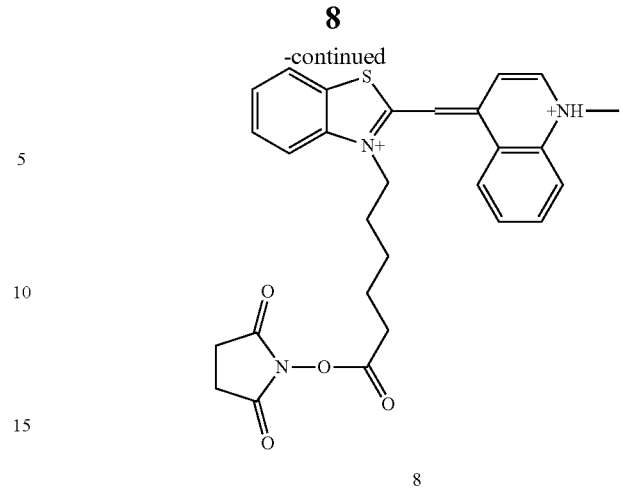

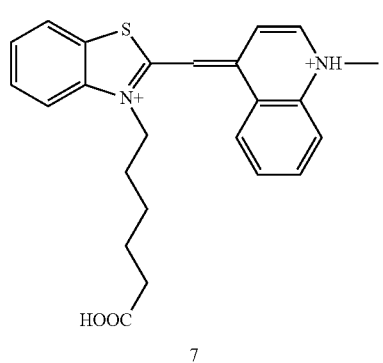

Figure 3:
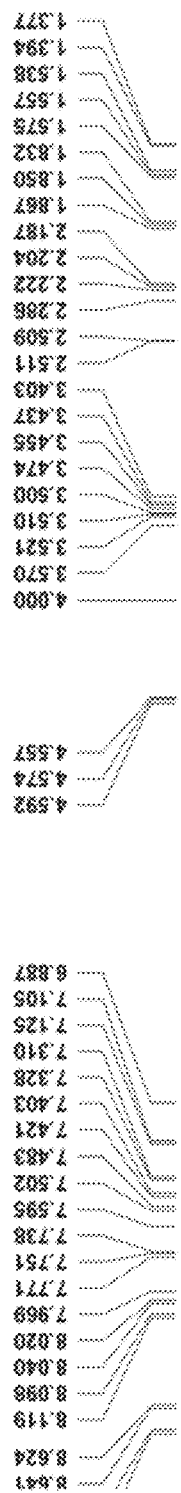
FIG. 3 is an H NMR spectrum of compound 7 according to the disclosure.
Figure 3:
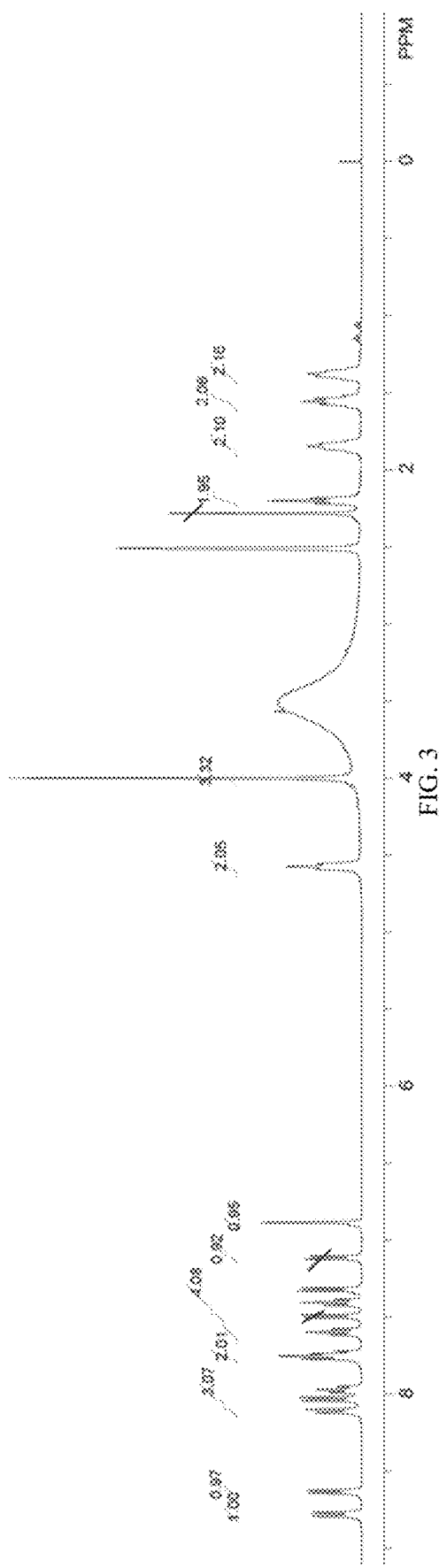
Figure 4:
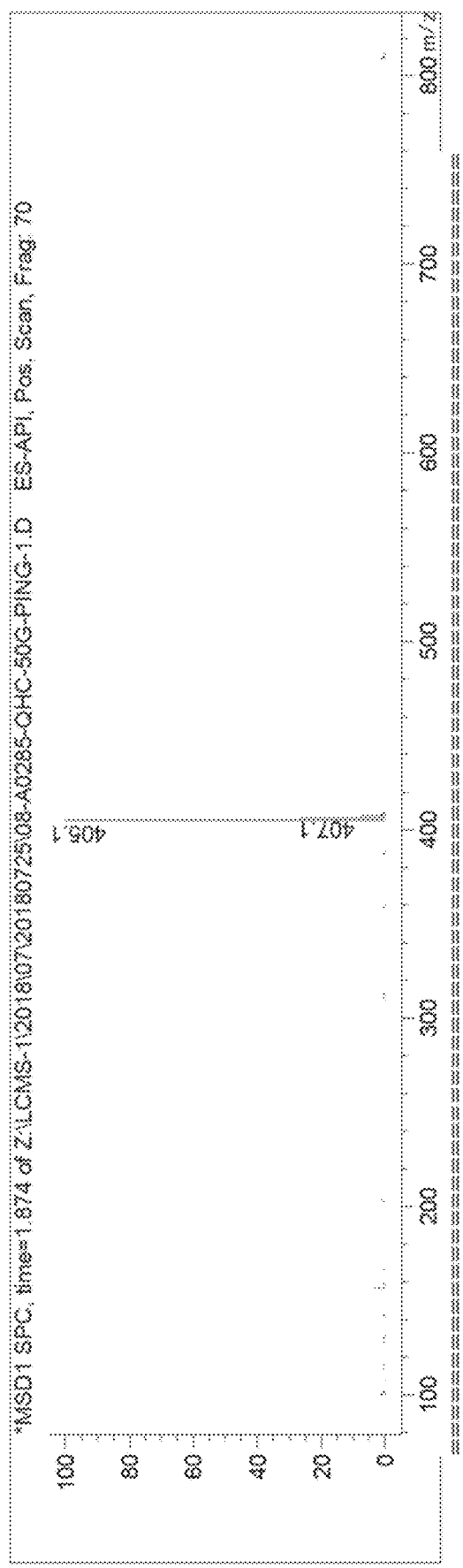
FIG. 4 is a mass spectrum of compound 7 according to the disclosure.

The H NMR spectrum of the compound 7 is shown in FIG. 3. Test conditions are as follows: $^1$H NMR (400 MHz, d$_6$-DMSO);

The mass spectrum of the compound 7 is shown in FIG. 4, ESI-MS: experimental value m/z=405.1.

S4, Synthesis of Compound 8

25 g of compound 7 and 15 g of 2-succinylimido-1,1,3,3-tetramethylurea tetrafluoroborate (TSTU for short) were added into 625 mL of andydrous acetonitrile, 12.5 mL of triethylamine was dropwise added at room temperature, the above materials reacted for 4 h at room temperature after dropwise addition was ended, TLC detection was performed, and the reaction was ended to obtain an acetonitrile solution of compound 8, a reaction equation is as follows:

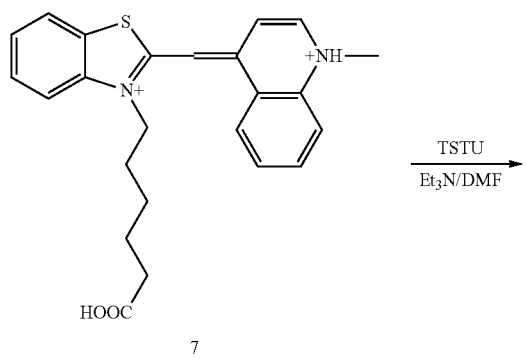

S5, Synthesis of Compound 11

15 g of compound 9 was dissolved into 150 mL of DMF, TSTU was added three times under the condition of less than 20° C., the addition amounts of TSTU each time in three times were respectivley 5 g, 5 g and 4 g, the above materials were stirred for 30 min, 9.6 g of triethanolamine was dropwise added, the tempeature was controlled at 20° C.-25° C., the above mateirals were stirred for 30 min, then TLC deteciton (dichloromethane/mathonal=5:1, a volume ratio) was performed, the reaction was completed, 1.2 g of ethanediamine was slowly dropwise added at 20-25° C. for 2 h until dropwise addition was ended, the above materials reacted for 12 h, TLC deteciton (dichloromethane/mathonal=5:1, a volume ratio) was performed, the reaction was completed, and a mixed solution in which a volume ratio of dichoromethane to mathanol is 5:1 was loaded on a silicagel column to obtain 14.5 g of red solid, that is, compound 11, with a yield of 92%; a reaction equation is as follows:

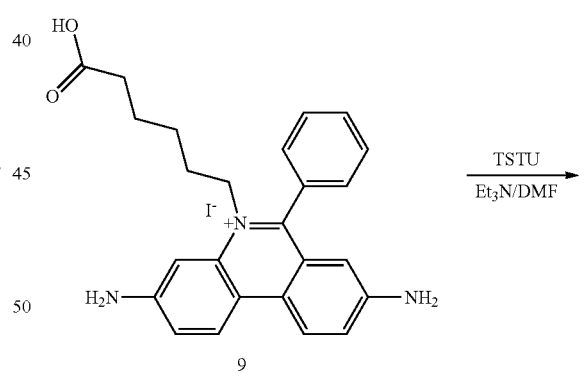

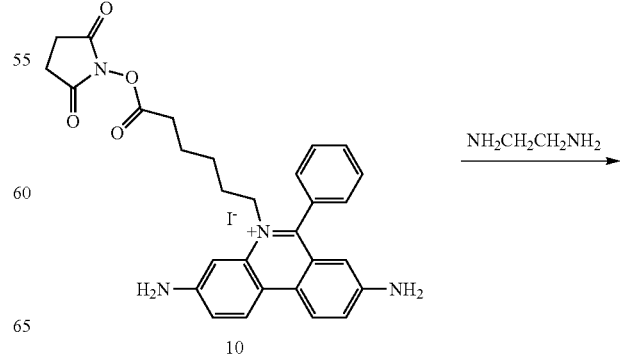

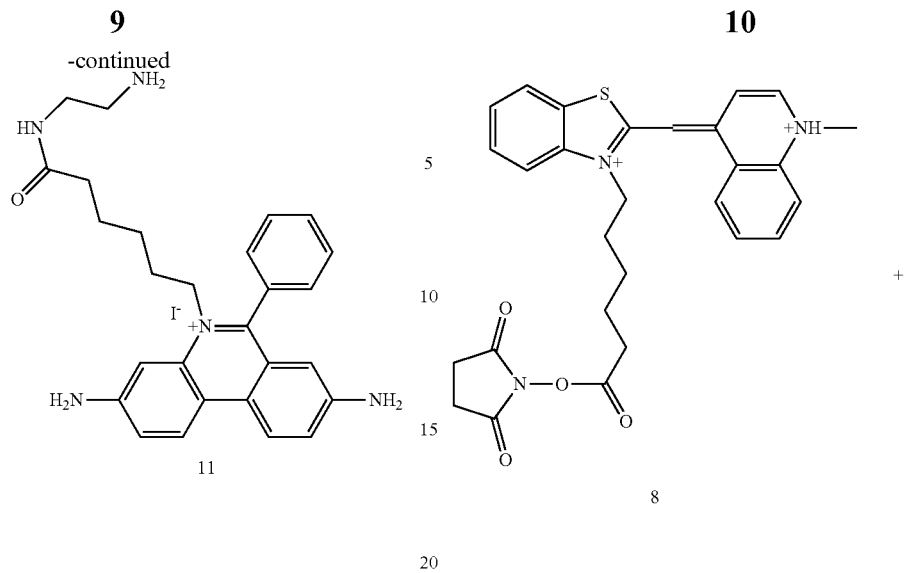

11

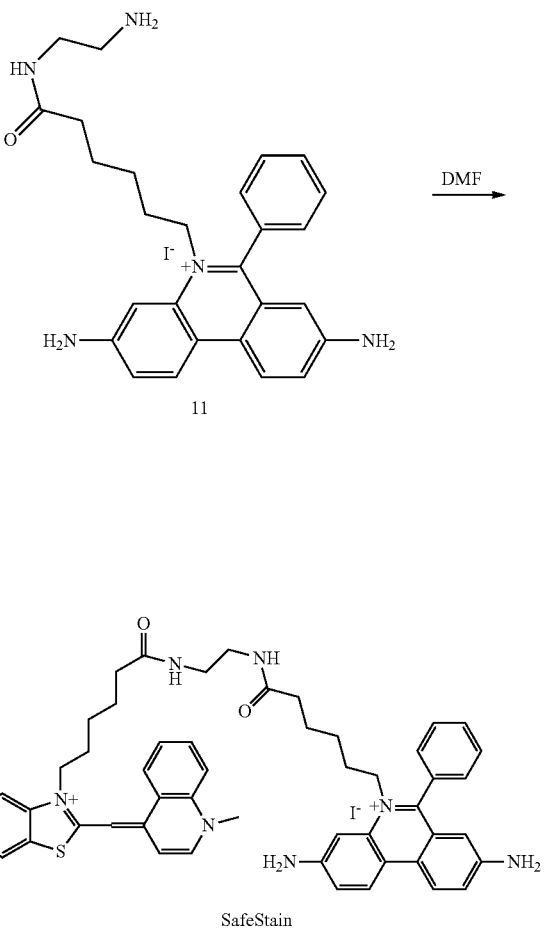

Figure 5:
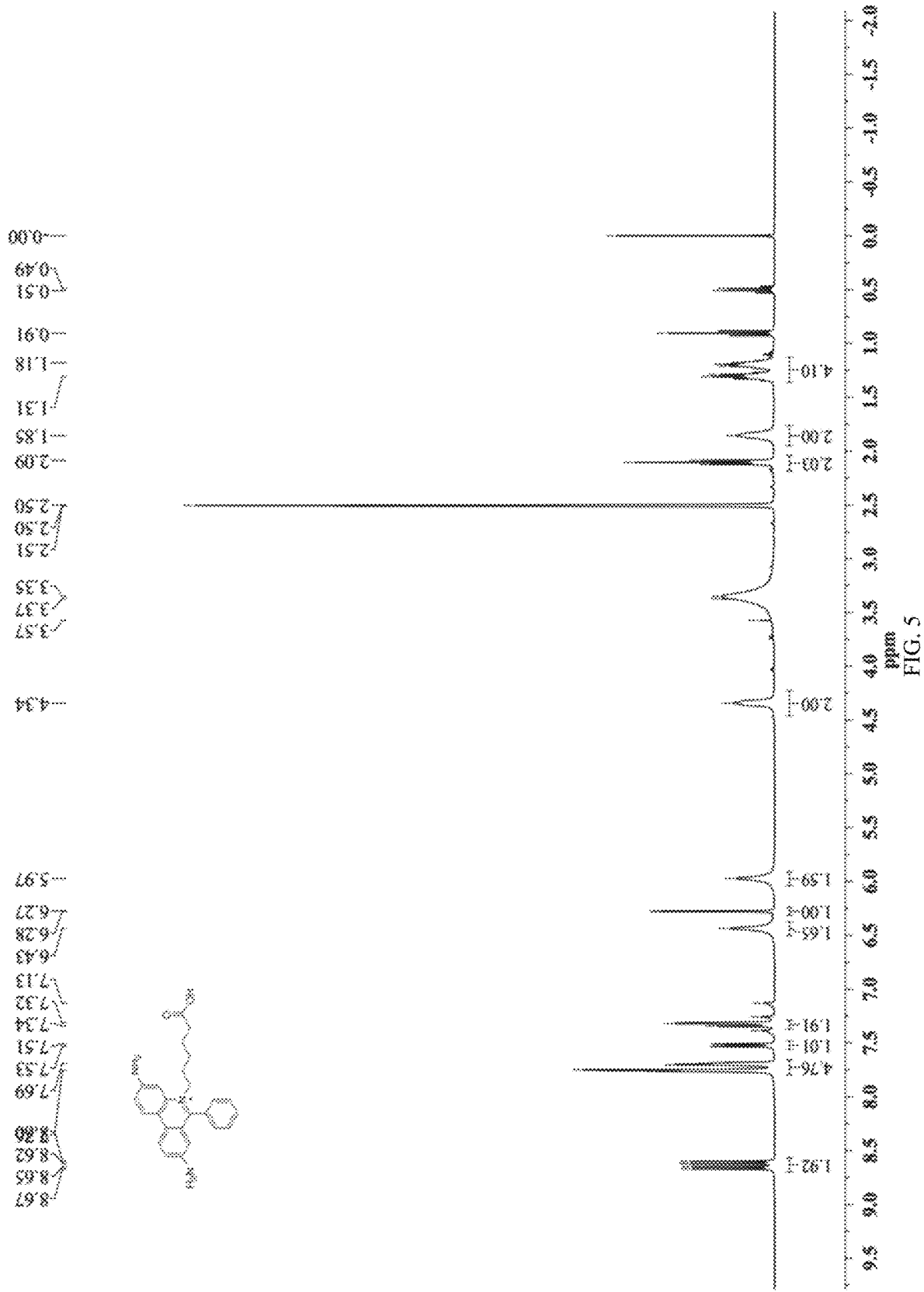
FIG. 5 is an H NMR spectrum of compound 9 according to the disclosure.
Figure 6:
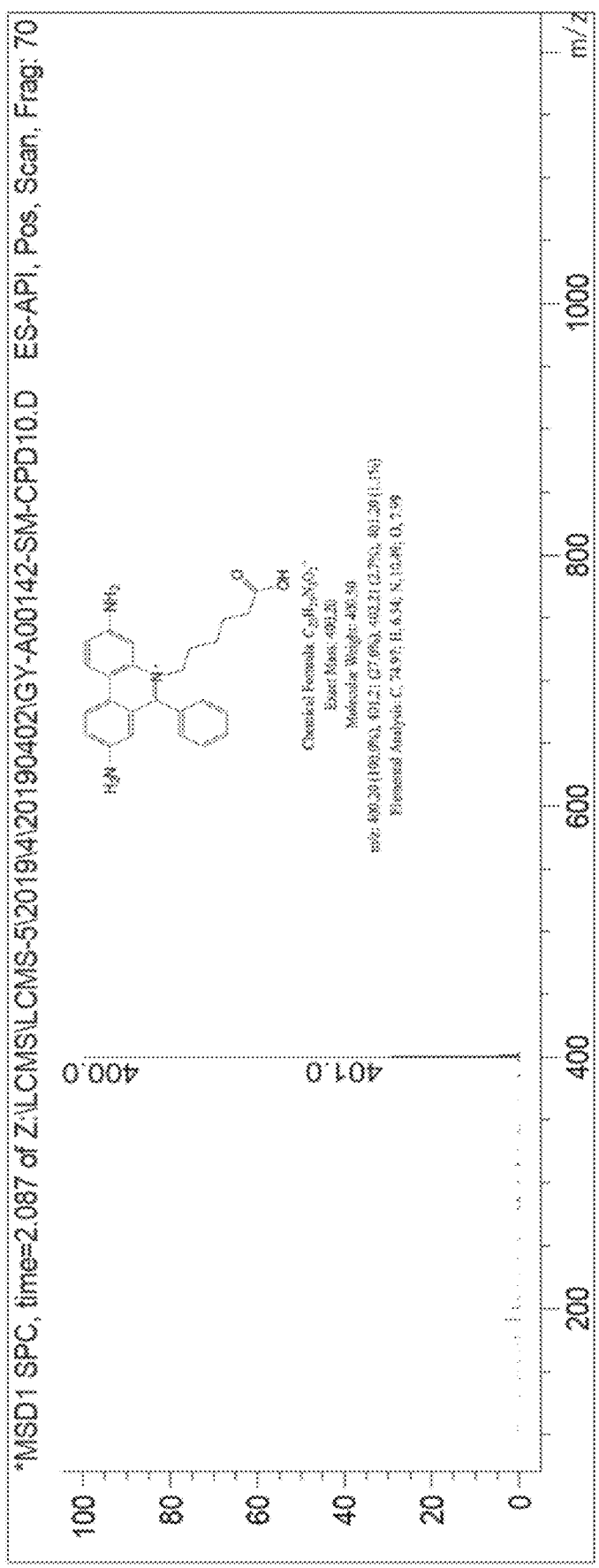
FIG. 6 is a mass spectrum of compound 9 according to the disclosure.

The H NMR spectrum of the compound 11 is shown in FIG. 7. Test conditions are as follows: $^1$H NMR (400 MHz, $d_6$-DMSO);

The mass spectrum of the compound 11 is shown in FIG. 8, ESI-MS: experimental value m/z=443.1;

wherein, compound 9 was obtained by using a method described in Bioorganic & Medicinal Chemistry Letters, Volume 17, Issue 8, 15 Apr. 2007, Pages 2267-2273, with a reaction yield of 87%, the H NMR spectrum of the compound 9 is shown in FIG. 5: ($^1$H NMR, $d_6$-DMSO) δ (ppm) 8.53-8.61 (dd, 2H), 7.75 (m, 3H), 7.54-7.59 (m, 3H), 7.35 (m, 2H), 6.45 (s, 1H), 4.49-4.51 (m, 2H), 2.18-2.21 (m, 2H), 1.52-1.21 (m, 6H), and the mass spectrum of the compound 9 is shown in FIG. 6, ESI-MS: experimental value m/z=400.17, found 401.0 (M$^+$));

S6, Synthesis of Fluorescent Dye 14.5 g of compound 11 was dissolved with DMF and then directly added into the acetonitrile solution of compound 8 to react for 16 h, TLC detection was performed, the reaction was completed, 500 mL of water was added into a reaction solution, supernate was discarded after stirring for 10 min, the above oeprations were repeated twice, a mixed solution in which a volume ratio of dichloromethane to methanol was 5:1 was added for washing, then 40 mL of water was added for liquid separation, a red and viscous product was separated out, water was discarded, the separated red and viscous product was loaded on the silicagel column with the mixed solution in which the volume ratio of dichloromethane to methanol was 5:1 to obtain 17.5 g of red solid, that is, the fluorescent dye with phenanthridine and benzothiazole conjugated, namely, SafeStain, with 49%. The HPLC test result of the fluorescent dye SafeStain is shown in FIG. 9A and FIG. 9B; a reaction equation is as follows:

Example 3

Applicaion of the Fluorescent Dye in Example 1

I. Polymerase Chain Reaction (PCR) Experiment

The fluorescent dyes respectively adopted SYBR Green and the fluorescent dye SafeStain in example 1, and selected upstream and downstream primers were respectively as follows:

Upstream primer: CAACCGGTCCCCACGTTGCC
Downstream primer: AACGGCTGG-GAGAACCTGGTTCTCAATGTA A PCR reaction system is shown in Table 1

TABLE 1

50 μL of PCR reaction system

| Components | Volume | Final concentration |
|---|---|---|
| 2× SYBR Green | 25 μL | 1× |
| DNA template | 2 μL | 10 ng |
| 10 μM upstream primer | 1 μL | 0.2 μM |
| 10 μM downstream primer | 1 μL | 0.2 μM |
| Final volume (water added) | 50 μL | |

PCR reaction conditions were as follows: pre-denature for 30 s at 95° C., denature for 10 s at 95° C., anneal for 10 s at 55° C.-65° C., and extend for 30 s, 40 cycles in total.

PCR amplification was performed with a pGDR11 KOD-RS plasmid as a template and by using upstream/downstream primers. An amplified target sequence is shown in SEQ ID NO:1.

In the above PCR reaction system, the whole PCR process was monitored in real time by fluorescence signal accumulation, fluorescence signals were collected every cycle, and an electrophoretogram of a real-time fluorescence quantative PCR amplification product was obtained by using the numer of cycles as an abscissa and fluorescence intensity as an ordinate, as shown in FIG. 10. It can be seen from FIG. 10 that under the conditions of identical fluorescence dye concentraiton, identical DNA concentration and identical cycle number, the fluorescence intensity generated by the SafeStain fluorescence dye in example 1 after binding to DNA is stronger than the fluorescence intensity generated by SYBR Green fluorescence dye after binding to DNA, indicating that the fluorescence dye synthesized in the disclosure has a high DNA detection sensitivity and is more suitable for real-time quantantive PCR reaction of fluorescence dyes and detection of DNA.

II. Agarose Gel Electrophoresis Experiment

Experimental Materials and Reagents:

Experimenal Sample: Plasmid DNA, DNA Label (1 kb DNA Ladder, 100 bp DNA Ladder and 100 bp Plus DNA Ladder)

Experimental reagents: TAE electrophoresis buffer (24.2 g of Tris, 5.71 mL of glacial acetic acid, 2.92 g of EDTA, 1.6 g of NaOH, pH8.0, 5000 mL of final volume), a bromophenol blue indicator, 1% agarose gel, and 1% agarose gel electrophoresis dye Experimental instruments: a tianneng electrophoresis apparatus (100V), a pipette (0.5~ 10 μl), and a UV Gel imager.

Experimental Steps:

(1) making a gel: 0.2 g of agarose was dissolved into 20 mL of TAE electrophoresis buffer, heated until the agarose was completely melted, the melted agarose solution was placed at room temperature, 2 μL of gel electrophoresis dye was added at 40° C.-50° C., and the above materials were uniformly mixed;

(2) pouring the gel: the made agarose gel was slowly poured into a gel-making tray, and bubbles were avoided; a sample application comb was verticaly placed at one end of an electrophoresis gel mould, which was distanced from the bottom of the tray by 1 mm; during the placement, keep steady and smooth, and do not sway;

(3) placing the gel: after the gel body was solidified, the sample application comb was slowly and vertically pulled out upward, do not overexert;

(4) the agarose gel was put into an electrophoresis tank, and the TAE electrophoresis buffer was added, so that the liquid level of the electrophoresis buffer was higher than that of the gel by 1-2 mm;

(5) 1 μL of bromophenol blue was mixed with 2 μL of DNA specimen to obtain a DNA sample mixed with a bromophenol blue indicator, and the obtained DNA sample was added into a sample application well;

(6) the electrophoresis tank was covered, and a power source was turned on, so that DNA moved from a negative electrode to a positive electrode, and constant-voltage elelctrophoresis was performed at a constant voltage of 100V-120V;

(7) after DNA strips were distanced from the sample application wells by 1-2 cm, the power source was turned off, the gel was taken out and observed respectively under the ultraviolet scenograph and the blue light gel imager.

Electrophoresis results are shown in FIG. 11. It can be seen from FIG. 11 that whether it is observed under the UV Gel imager or the blue light gel imager, strips are clearly isolated and the sensitivities are very high. Therefore, the fluorescent dye of the disclosure can realize nucleic acid electrophoresis staining under the UV Gel imager and the blue light gel imager at the same time, and has high sensitivity, so as to solve the problems in the prior art that the fluorescent dye cannot be simultaneously applied to the UV Gel imager and the blue light gel imager.

The above descriptions are only preferred embodiments of the disclosure, but not limiting the disclosure. Any amendments, equivalent replacements, modifications and the like made withtin the spirit and principle of the disclosure should be included within the protective scope of the disclosure.

We claim:

1. A fluorescent dye with phenanthridine and benzothiazole conjugated, wherein the fluorescent dye has the following structural formula:

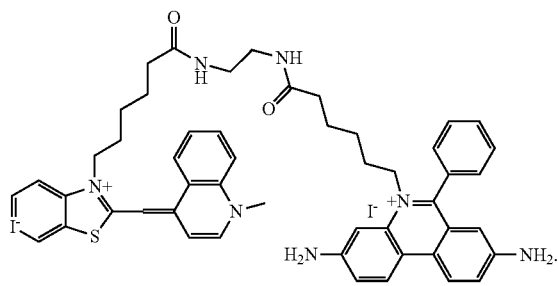

2. A method for preparing the fluorescent dye with phenanthridine and benzothiazole conjugated according to claim 1, comprising the following steps:

S1, reacting a compound of formula 1 with methyl iodide for 4 h at 210° C. under the protection of nitrogen to prepare a compound of formula 3;

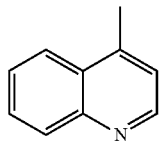
1

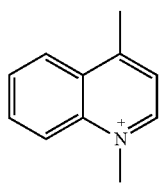
3

S2, dissolving a compound of formula 4 and 6-bromo-1-hexanoic acid into absolute ethyl alcohol under the protection of nitrogen, heating to 35° C. under the protection of nitrogen, and reacting for 4 h so as to prepare a compound of formula 6;

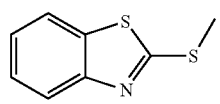
4

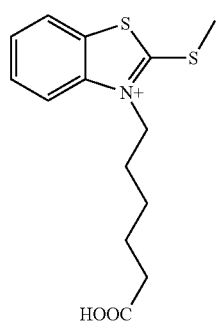
6

S3, dissolving the compound of formula 3 and the compound of formula 6 into ethyl alcohol, adding triethylamine under the protection of nitrogen, and reacting for 3 h to prepare a compound of formula 7;

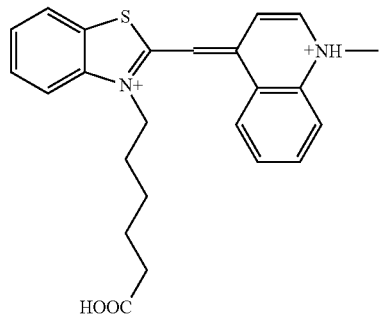
7

S4, dissolving the compound of formula 7 and 2-succinylimido-1,1,3,3-tetramethylurea tetrafluoroborate into acetonitrile, adding triethylamine, and reacting for 4 h to prepare an acetonitrile solution of a compound of formula 8;

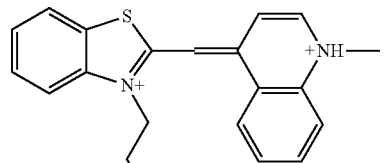
8

S5, dissolving a compound of formula 9 into dimethyl formamide (DMF), adding 2-succinylimido-1,1,3,3-tetramethylurea tetrafluoroborate, stirring for 30 min, then adding triethanolamine, reacting for 30 min at 20-25° C., adding ethanediamine, and reacting for 12-16 h to prepare a compound of formula 11; and

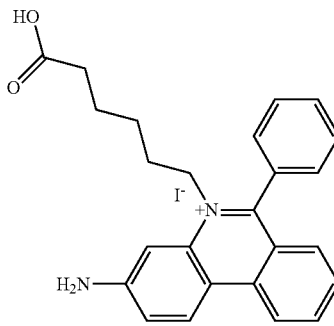
9

-continued
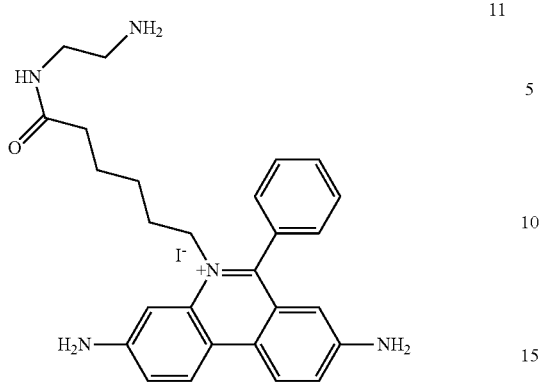
11
S6, dissolving the compound of formula 11 into DMF, adding the acetonitrile solution of the compound of formula 8, and reacting for 12-16 h to obtain the fluorescent dye with phenanthridine and benzothiazole conjugated.
* * * * *